(12) United States Patent
Lai et al.

(10) Patent No.: US 7,980,757 B2
(45) Date of Patent: Jul. 19, 2011

(54) BONDING STRENGTH MEASURING DEVICE

(75) Inventors: Yi-Shao Lai, Taipei County (TW);
Tsung-Yueh Tsai, Kaohsiung (TW);
Hsiao-Chuan Chang, Kaohsiung (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 254 days.

(21) Appl. No.: 12/350,643

(22) Filed: Jan. 8, 2009

(65) Prior Publication Data
US 2009/0175312 A1    Jul. 9, 2009

(30) Foreign Application Priority Data

Jan. 9, 2008  (TW) .............................. 97100870 A

(51) Int. Cl.
*G01K 1/00*  (2006.01)
*G01N 25/00*  (2006.01)

(52) U.S. Cl. .................. 374/5; 374/57; 374/53; 374/46; 374/143; 73/150 A

(58) Field of Classification Search .................... 374/46, 374/5, 57, 53, 143; 73/150 A
See application file for complete search history.

(56) References Cited

U.S. PATENT DOCUMENTS

| | | | | |
|---|---|---|---|---|
| 3,733,887 A | * | 5/1973 | Stanley et al. | 374/44 |
| 4,604,572 A | * | 8/1986 | Horiuchi et al. | 324/760 |
| 5,176,028 A | * | 1/1993 | Humphrey | 73/150 A |
| 6,117,695 A | * | 9/2000 | Murphy et al. | 438/15 |
| 2003/0072349 A1 | * | 4/2003 | Osone et al. | 374/43 |
| 2006/0045165 A1 | * | 3/2006 | Chan et al. | 374/43 |
| 2008/0095211 A1 | * | 4/2008 | You et al. | 374/45 |

* cited by examiner

*Primary Examiner* — Lisa M Caputo
*Assistant Examiner* — Mirellys Jagan
(74) *Attorney, Agent, or Firm* — J.C. Patents

(57) ABSTRACT

A bonding strength measuring device for measuring the bonding strength between a substrate and a molding compound disposed on the substrate is provided. The measuring device includes a heating platform, a heating slide plate, and a fixing bracket. The heating platform has a first heating area and a first replaceable fixture. The substrate is disposed on the first heating area, and the first replaceable fixture is used to fix the substrate and has an opening exposing the molding compound. The heating slide plate has a second heating area and a second replaceable fixture. The second heating area is used to heat the molding compound, and the second replaceable fixture has a cavity for accommodating the molding compound. The fixing bracket is used to fix the heating slide plate above the heating platform.

6 Claims, 3 Drawing Sheets

BONDING STRENGTH MEASURING DEVICE

CROSS-REFERENCE TO RELATED APPLICATION

This application claims the priority benefit of Taiwan application serial no. 97100870, filed on Jan. 9, 2008. The entirety of the above-mentioned patent application is hereby incorporated by reference herein and made a part of specification.

BACKGROUND OF THE INVENTION

1. Field of the Invention

The present invention generally relates to a bonding strength measuring device, in particular, to a device for measuring the bonding strength between a molding compound and a substrate.

2. Description of Related Art

Generally, after packaging, most electronic products will undergo finished product tests, such as aging test, electrical property test, pull test, solder ball shear stress test, and bonding strength test, so as to ensure the product quality and yield. Especially for small-scale and portable electronic products, internal semiconductor devices may easily be damaged due to shocks caused by collision or fall-off. Moreover, when the bonding between the molding compound and the substrate is aggravated, steam or hot gas may infiltrate through cracks into the semiconductor devices inside the molding compound, thus shortening the service life of the electronic products.

To exactly master the reliability of the electronic products and make the same meet certain specifications, a destructive experiment is usually performed on the bonding strength between a molding compound and a substrate, and analyzable numerical values are obtained through measurement. For example, a force is horizontally exerted on a molding compound by a push broach, and numerical values when the molding compound is destructed and detached from the substrate are measured. The higher the numerical values are, the greater the bonding strength is; on the contrary, the lower the numerical values are, the weaker the bonding strength is. However, the above destructive experiment does not consider the thermal stress effect, thus deviating from actual applications of the electronic products. Therefore, it is the problem in urgent need of solutions to improve the measurement of the bonding strength between the molding compound and the substrate.

SUMMARY OF THE INVENTION

Accordingly, the present invention is directed to a bonding strength measuring device, for simulating and measuring the bonding strength between a molding compound and a substrate when heated.

The present invention provides a bonding strength measuring device suitable for measuring the bonding strength between a substrate and a molding compound disposed on the substrate. The measuring device includes a heating platform, a heating slide plate, and a fixing bracket. The heating platform has a first heating area and a first replaceable fixture. The substrate is disposed on the first heating area, and the first replaceable fixture is fixed on the substrate and has an opening exposing the molding compound. The heating slide plate has a second heating area and a second replaceable fixture. The second heating area is used to heat the molding compound, and the second replaceable fixture has a cavity for accommodating the molding compound. The fixing bracket is used to fix the heating slide plate above the heating platform.

In an embodiment of the present invention, the heating slide plate has an accommodation groove and a plurality of slide ways disposed along a pushing direction, the molding compound moves along the accommodation groove into the cavity, and the fixing bracket has a plurality of pillars moving along the slide ways.

In an embodiment of the present invention, the fixing bracket is further provided with a plurality of fixing plates for supporting the heating slide plate on the pillars.

In an embodiment of the present invention, the pillars are threaded rods, and the fixing plates are adjustably locked on the pillars for adjusting height of the heating slide plate.

In an embodiment of the present invention, a manometer is further connected to the heating slide plate, for measuring the pressure in the pushing direction.

In an embodiment of the present invention, the first heating area is an electrified device with a heating coil and a heat conductor, and the second heating area is an electrified device with a heating coil and a heat conductor.

Thereby, the improved bonding strength measuring device provided by the present invention may precisely measure the bonding strength between the molding compound and the substrate when heated, such that variations of the thermal stress effect to the bonding strength can be truly simulated to serve as important comparison references.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
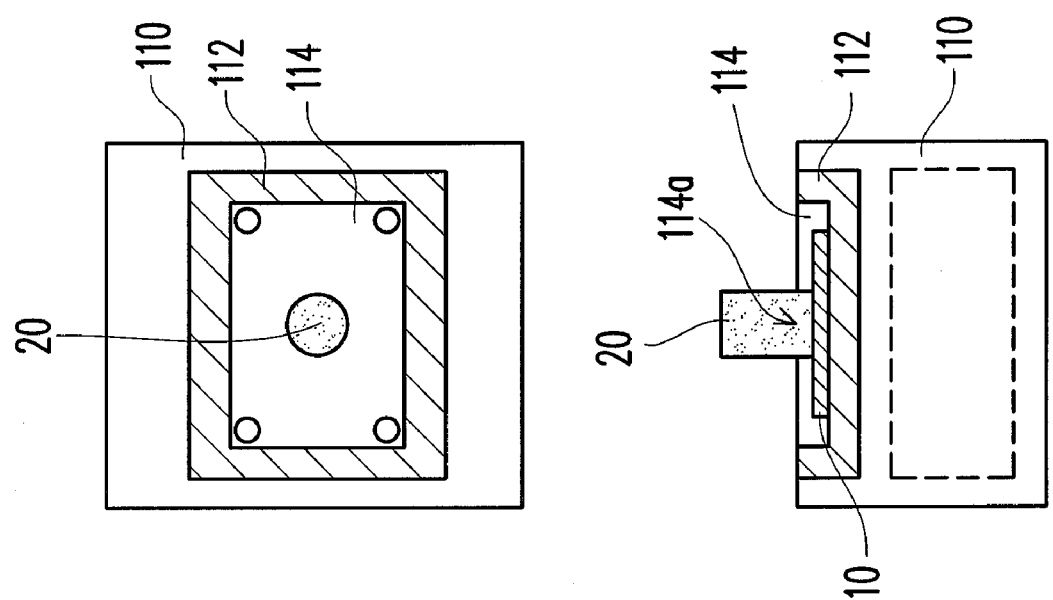
FIG. 1 respectively shows a schematic top view and a schematic side view of a heating platform.

Reference will now be made in detail to the present embodiments of the invention, examples of which are illustrated in the accompanying drawings. Wherever possible, the same reference numbers are used in the drawings and the description to refer to the same or like parts.

Figure 2:
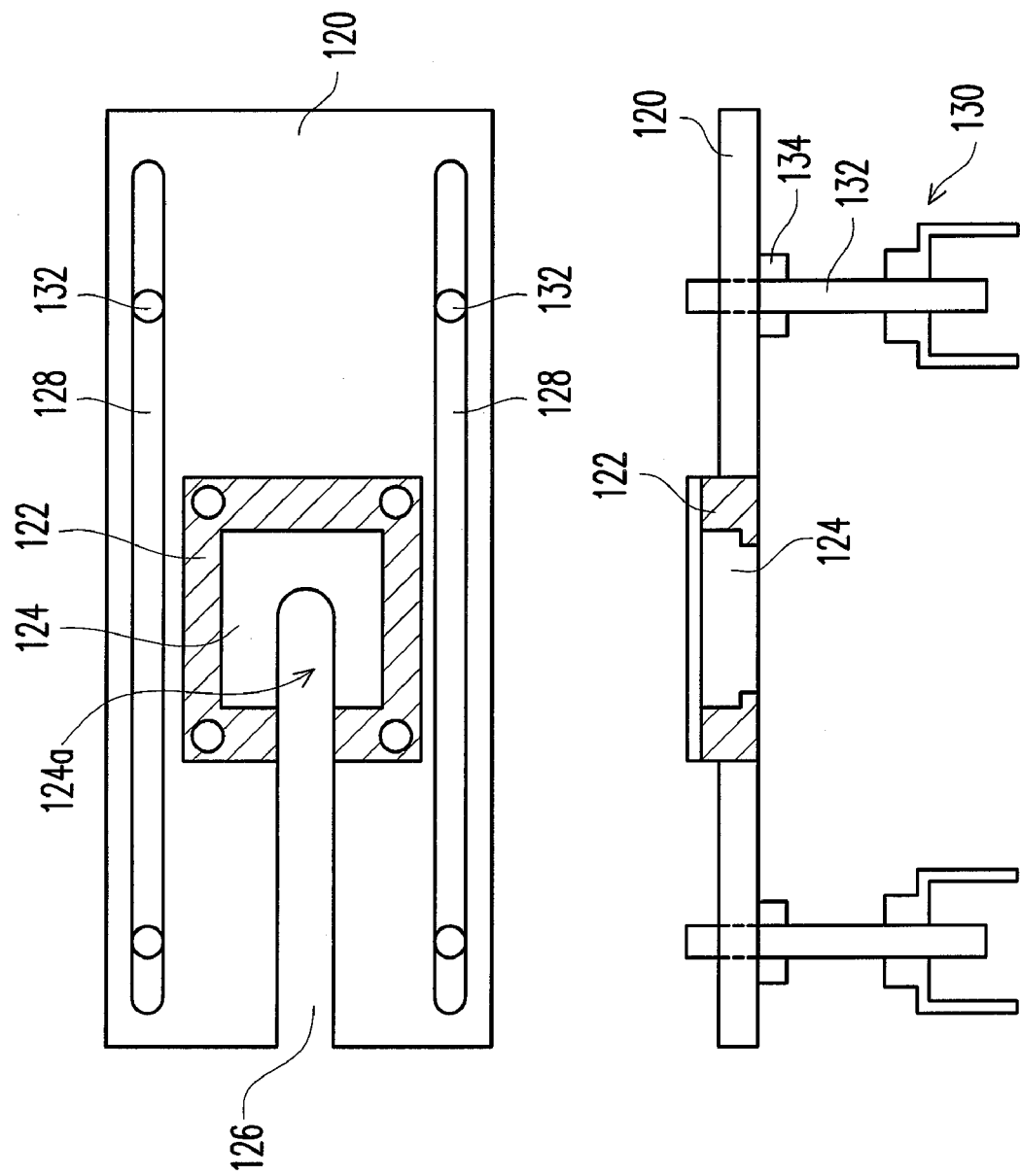
FIG. 2 respectively shows a schematic top view and a schematic side view of a heating slide plate and a fixing bracket.
Figure 3:
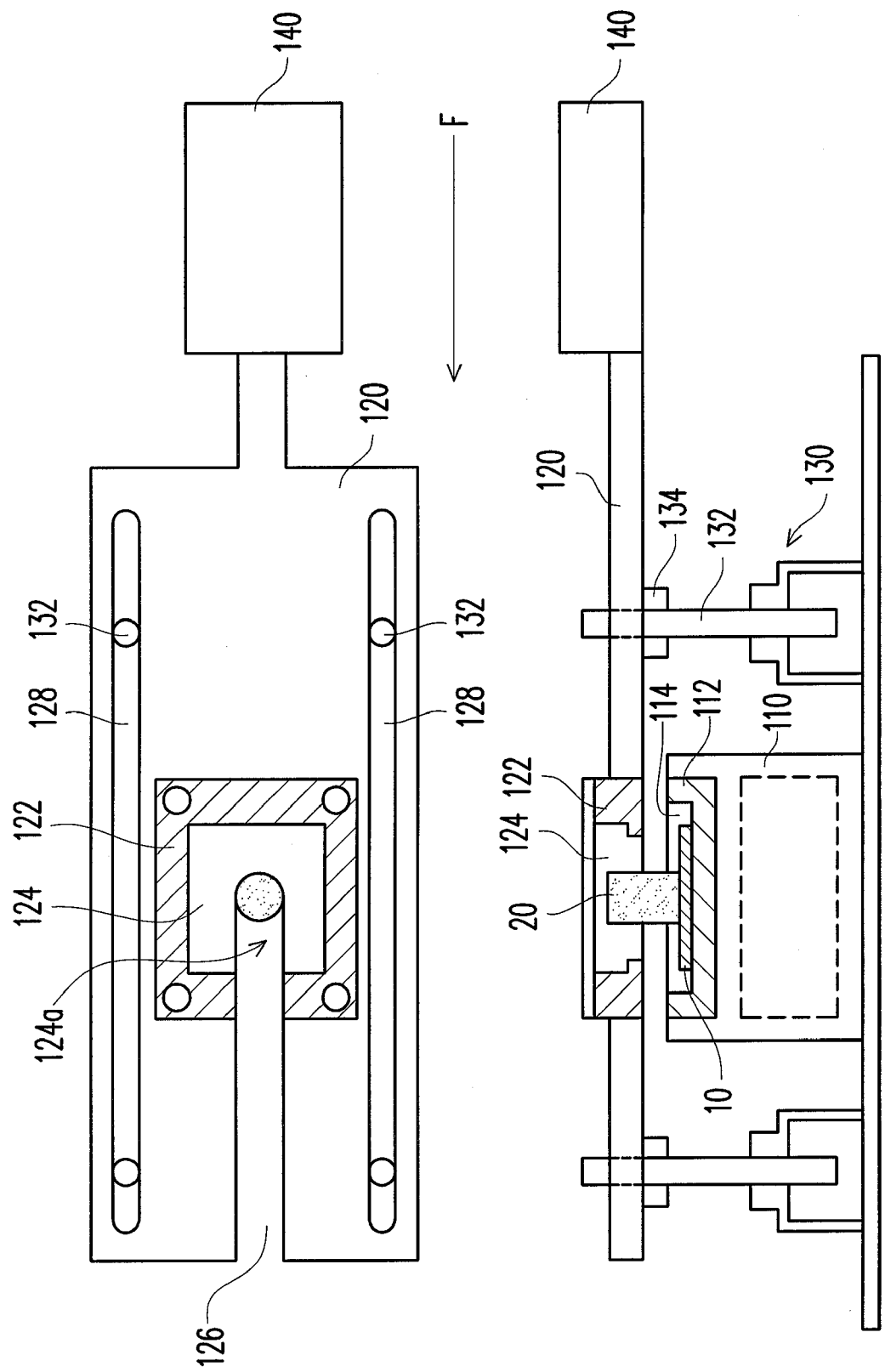
FIG. 3 respectively shows a schematic assembly view and a schematic operation view of a bonding strength measuring device according to an embodiment of the present invention.

FIG. 1 respectively shows a schematic top view and a schematic side view of a heating platform, FIG. 2 respectively shows a schematic top view and a schematic side view of a heating slide plate and a fixing bracket, and FIG. 3 respectively shows a schematic assembly view and a schematic operation view of a bonding strength measuring device according to an embodiment of the present invention.

Referring to FIGS. 1 and 2, the bonding strength measuring device mainly includes a heating platform 110, a heating slide plate 120, and a fixing bracket 130. The heating platform 110 has a first heating area 112 and a first replaceable fixture 114. The substrate 10 is disposed on the first heating area 112, and the replaceable fixture 114 is fixed on the substrate 10. The first heating area 112 is used to heat the substrate 10 to a predetermined experimental temperature, so as to simulate thermal stress variations of the substrate 10 when heated in actual circumstances.

In this embodiment, the first heating area 112 is, for example, an electrified device provided with a heating coil and a heat conductor, for controlling the current input into the heating coil to heat up the heat conductor. When disposed on the heat conductor of the first heating area 112, the substrate 10 is uniformly heated by the heat conductor to reach the predetermined experimental temperature, for example, 90±20° C. or 210±20° C. The first replaceable fixture 114 may be a single fixing plate locked to a mount of the heating platform 110 by screws, and has an opening 114a exposing the molding compound 20. The molding compound 20 is in the shape of a cylinder or a flat-topped cone (commonly referred to as a pudding shape). In addition, the bottom of the molding compound 20 is bonded to the substrate 10, and the top thereof protrudes above the first replaceable fixture 114. As the bonding strength between the molding compound 20 and the substrate 10 should consider thermal stress variations, the molding compound 20 and the substrate 10 must be heated together to simulate the bonding strength in actual circumstances.

Referring to FIG. 2, the heating slide plate 120 has a second heating area 122 and a second replaceable fixture 124. The second replaceable fixture 124 is fixed on the second heating area 122, and has a cavity 124a for accommodating the molding compound. The second heating area 122 is used to heat the molding compound 20 in FIG. 1 to a predetermined experimental temperature, so as to simulate thermal stress variations of the molding compound 20 when heated in actual circumstances.

In this embodiment, the second heating area 122 is, for example, an electrified device provided with a heating coil and a heat conductor, for controlling the current input into the heating coil to heat up the heat conductor. When positioned in the cavity 124a of the second replaceable fixture 124, the molding compound 20 is heated by the heat conductor of the second heating area 122 to reach the predetermined experimental temperature, for example, 120-230° C. The second replaceable fixture 124 may be a single fixing plate locked to a body of the heating slide plate 120 by screws. The cavity 124a of the second replaceable fixture 124 has a cylindrical inner wall in conformity with the surface of the molding compound 20, such that when a force is applied by the heating slide plate 120 on the molding compound 20, a uniform shear stress can be simulated.

Further, referring to FIGS. 2 and 3, the heating slide plate 120 further has an accommodation groove 126 and a plurality of slide ways 128 disposed along a pushing direction F. The molding compound 20 moves along the accommodation groove 126 into the cavity 124a, and the fixing bracket 130 has a plurality of pillars 132 moving along the slide ways 128, such that the heating slide plate 120 may be driven by a force to move along the pushing direction F. The fixing bracket 130 is used to fix the heating slide plate 120 above the heating platform 110, and the fixing bracket 130 further has a plurality of fixing plates 134 for supporting the heating slide plate 120 on the pillars 132. The pillars 132 are, for example, threaded rods, and the fixing plates 134 are, for example, adjustable locking members, locked on the pillars 132 for adjusting the height of the heating slide plate 120.

Referring to FIG. 3, in order to measure the bonding strength between the molding compound 20 and the substrate 10, a manometer 140 is connected to the heating slide plate 120 to measure the pressure in the pushing direction F. The whole process of the test is introduced as follows. First, the molding compound 20 disposed on the substrate 10 is placed between the heating platform 110 and the heating slide plate 120, and the height of the heating slide plate 120 is adjusted to make the molding compound 20 right located in the cavity 124a. Next, the substrate 10 and the molding compound 20 are respectively heated to a predetermined experimental temperature. Afterward, a force is exerted in the pushing direction F, so as to perform a destructive experiment on the molding compound 20, and analyzable numerical values are measured by the manometer 140. As the destructive experiment has already considered the thermal stress effect, the experimental state is in accordance with actual applications of electronic products, and thus the desired numerical values can be truly simulated.

In view of the above, the improved bonding strength measuring device provided by the present invention may precisely measure the bonding strength between the molding compound and the substrate when heated, such that variations of the thermal stress effect to the bonding strength can be truly simulated to serve as important comparison references.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A bonding strength measuring device, for measuring the bonding strength between a substrate and a molding compound disposed on the substrate, the measuring device comprising:
    a heating platform, comprising a first heating area and a first replaceable fixture, wherein the substrate is disposed on the first heating area, and the first replaceable fixture is fixed on the substrate and has an opening exposing the molding compound;
    a heating slide plate, comprising a second heating area and a second replaceable fixture, wherein the second heating area is used to heat the molding compound, and the second replaceable fixture has a cavity for accommodating the molding compound; and
    a fixing bracket, for fixing the heating slide plate above the heating platform, wherein the heating slide plate has an accommodation groove and a plurality of slide ways disposed along a pushing direction, the molding compound moves along the accommodation groove into the cavity, and the fixing bracket comprises a plurality of pillars moving along the slide ways.

2. The bonding strength measuring device according to claim 1, further comprising a manometer connected to the heating slide plate.

3. The bonding strength measuring device according to claim 1, wherein the first heating area is an electrified device with a heating coil and a heat conductor.

4. The bonding strength measuring device according to claim 1, wherein the second heating area is an electrified device with a heating coil and a heat conductor.

5. The bonding strength measuring device according to claim 1, wherein the fixing bracket further comprises a plurality of fixing plates for supporting the heating slide plate on the pillars.

6. The bonding strength measuring device according to claim 5, wherein the pillars are threaded rods, and the fixing plates are adjustably locked on the pillars for adjusting height of the heating slide plate.

* * * * *